United States Patent [19]

Fischer

[11] 3,935,001

[45] Jan. 27, 1976

[54] HERBICIDE MIXTURES OF URACIL, A CARBAMATE AND A PYRIDAZONE

[75] Inventor: Adolf Fischer, Mutterstadt, Germany

[73] Assignee: BASF Aktiengesellschaft, Ludwigshafen (Rhine), Germany

[22] Filed: July 30, 1974

[21] Appl. No.: 493,115

Related U.S. Application Data

[62] Division of Ser. No. 348,085, April 4, 1973.

[30] Foreign Application Priority Data

Apr. 13, 1972   Germany............................ 2217698

[52] U.S. Cl..................................... 71/92; 71/111
[51] Int. Cl.² ........................................... A01N 9/22
[58] Field of Search................................ 71/92, 111

[56] References Cited
UNITED STATES PATENTS

| | | | |
|---|---|---|---|
| 3,235,363 | 2/1966 | Luckenbaugh et al. ................ | 71/92 |
| 3,436,207 | 4/1969 | Soboczenski ........................... | 71/92 |
| 3,551,477 | 12/1970 | Koenig et al. ..................... | 71/111 X |
| 3,692,820 | 9/1972 | Boroschewski et al. .......... | 71/111 X |
| 3,758,477 | 9/1973 | Zeidler et al. ..................... | 71/92 X |
| 3,810,751 | 5/1974 | Fischer et al. ......................... | 71/92 |

*Primary Examiner*—Lewis Gotts
*Assistant Examiner*—Catherine L. Mills
*Attorney, Agent, or Firm*—Johnston, Keil, Thompson & Shurtleff

[57] ABSTRACT

Herbicidal mixtures of a three component mixture of (a) 3-cyclohexyl-5,6-trimethylene uracil; (b) 3-methoxycarbonylaminophenyl-N-(3'-methylphenyl)-carbamate, and (c) 1-phenyl-4-amino-5-chloropyridazone-(6).

1 Claim, No Drawings

HERBICIDE MIXTURES OF URACIL, A CARBAMATE AND A PYRIDAZONE

RELATED APPLICATION

This application is a division of my copending application Ser. No. 348,085, filed Apr. 4, 1973, the disclosure of which is incorporated herein by reference.

The present invention relates to herbicide compositions containing (a) 3-cyclohexyl-5,6-trimethylene uracil, (b) 3-methoxycarbonylaminophenyl-N-(3'-methylphenyl)-carbamate, and (c) 1-phenyl-4-amino-5-chloropyridazone-(6) at a weight ratio of 1–10:1–10:1–10.

The agents according to the invention may be used as solutions, emulsions, suspensions, oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e. g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e. g., kieselguhr, talc, clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

The new herbicides may be applied either pre- or post-emergence, and are particularly suited for controlling dicotyledonous seed weeds and monocotyledonous seed grasses in crops such as beet, spinach, potatoes, peas, beans and groundnuts.

EXAMPLE 1

In the greenhouse various plants were treated at a growth height of 3 to 11 cm with the following amounts of the following active ingredients and compositions thereof as dispersions:

I 3-cyclohexyl-5, 6-trimethylene uracil, 0.1, 1.0 and 1.2 kg/ha;

II 3-methoxycarbonylaminophenyl-N-(3'-methylphenyl)-carbamate, 0.1, 1.0 and 1.2 kg/ha;

III 1-phenyl-4-amino-5-chloropyridazone-(6), 0.1, 1.0 and 1.2 kg/ha;

I+II+III: 0.1+0.1+1.0, 0.1+1.0+0.1 and 1.0+0.1+0.1 kg/ha.

After 2 to 3 weeks it was ascertained that the compositions had a better herbicidal action than their individual components, combined with the same good crop plant compatibility.

The results are given below:

| Active ingredient kg/ha | I 0.1 | 1.0 | 1.2 | II 0.1 | 1.0 | 1.2 | III 0.1 | 1.0 | 1.2 |
|---|---|---|---|---|---|---|---|---|---|
| Crop plants: | | | | | | | | | |
| Beta vulgaris | 0 | 0 | 0 | 0 | 0 | 0 | 0 | 0 | 0 |
| Unwanted plants: | | | | | | | | | |
| Avena fatua | 2 | 30 | 34 | 2 | 20 | 23 | 1 | 10 | 11 |
| Bromus tectorum | 3 | 35 | 39 | 2 | 15 | 18 | 0 | 20 | 21 |
| Matricaria chamomilla | 4 | 40 | 43 | 5 | 35 | 39 | 5 | 40 | 44 |
| Setaria faberii | 3 | 35 | 38 | 3 | 20 | 23 | 1 | 20 | 24 |
| Sinapis arvensis | 12 | 65 | 73 | 8 | 75 | 81 | 13 | 35 | 39 |

0 = no damage
100 = complete destruction

| Active ingredient kg/ha | I + II + III 0.1+0.1+1.0 | I + II + III 0.1+1.0+0.1 | I + II + III 1.0+0.1+0.1 |
|---|---|---|---|
| Crop plants: | | | |
| Beta vulgaris | 0 | 0 | 0 |
| Unwanted plants: | | | |
| Avena fatua | 60 | 58 | 70 |
| Bromus tectorum | 60 | 56 | 65 |
| Matricaria chamomilla | 75 | 73 | 76 |
| Setaria faberii | 65 | 60 | 73 |
| Sinapis arvensis | 100 | 100 | 95 |

0 = no damage
100 = complete destruction

I claim:

1. A herbicide composition containing a herbicidally effective amount of a mixture of herbicides consisting of:
   a. 3-cyclohexyl-5,6-trimethylene uracil,
   b. 3-methoxycarbonylaminophenyl-N-(3'-methylphenyl)-carbamate, and
   c. 1-phenyl-4-amino-5-chloropyridazone-(6) in a weight ratio of a:b:c of 1–10: 1–10:1–10.

* * * * *